(12) United States Patent
Iyer et al.

(10) Patent No.: US 11,822,624 B2
(45) Date of Patent: Nov. 21, 2023

(54) SYSTEM AND METHOD FOR DIAGNOSING A DISEASE USING IMAGE CLASSIFICATION

(71) Applicant: Wipro Limited, Bangalore (IN)

(72) Inventors: Manjunath Ramachandra Iyer, Bangalore (IN); Chandrashekar Bangalore Nagaraj, Bangalore (IN); Shashidhar Soppin, Bangalore (IN)

(73) Assignee: Wipro Limited, Bangalore (IN)

( * ) Notice: Subject to any disclaimer, the term of this patent is extended or adjusted under 35 U.S.C. 154(b) by 490 days.

(21) Appl. No.: 17/192,923

(22) Filed: Mar. 5, 2021

(65) Prior Publication Data

US 2022/0207306 A1   Jun. 30, 2022

(30) Foreign Application Priority Data

Dec. 24, 2020   (IN) .............................. 202041056421

(51) Int. Cl.
*G06T 7/00*   (2017.01)
*G06F 18/24*   (2023.01)
(Continued)

(52) U.S. Cl.
CPC ............ *G06F 18/24* (2023.01); *G06F 18/213* (2023.01); *G06N 3/04* (2013.01); *G06N 3/08* (2013.01); *G06T 7/0016* (2013.01); *G16H 30/20* (2018.01); *G16H 30/40* (2018.01); *G16H 50/20* (2018.01); *A61B 6/032* (2013.01); *A61B 6/037* (2013.01); *G06T 2207/20081* (2013.01);
(Continued)

(58) Field of Classification Search
CPC ........ G16H 30/20; G16H 50/20; G16H 30/40; G06T 7/0016
See application file for complete search history.

(56) References Cited

U.S. PATENT DOCUMENTS

2020/0125852 A1\* 4/2020 Carreira ................. G06N 3/049
2020/0219262 A1\* 7/2020 Hsiao ................... G06V 10/764

OTHER PUBLICATIONS

Abiyev, R. et al., "Deep Convolutional Neural Networks for Chest Diseases Detection", Hindawi, 1-12 (2018).
(Continued)

*Primary Examiner* — Edward Park
(74) *Attorney, Agent, or Firm* — Finnegan, Henderson, Farabow, Garrett & Dunner, LLP (57) ABSTRACT

System and method for diagnosing a disease using image classification is provided. The method includes receiving diagnostic images associated with a subject. The diagnostic images comprise a first image and a second image captured at a first instance of time and at a second instance of time, respectively. The method further includes extracting feature maps from the first image and the second image, using a first pipeline and a second pipeline of stacked convolutional layers of a temporal convolutional neural network (CNN) model respectively. The method further includes identifying relevant feature maps from the feature maps using temporal CNN layer of the temporal CNN model, generating a concatenated feature map based on the relevant feature maps, determining an image class corresponding to the second image using fully connected layers of the temporal CNN model, and diagnosing the disease associated with the subject based on the image class.

20 Claims, 7 Drawing Sheets (51) Int. Cl.
- *G06N 3/04* (2023.01)
- *G06N 3/08* (2023.01)
- *G16H 50/20* (2018.01)
- *G16H 30/20* (2018.01)
- *G16H 30/40* (2018.01)
- *G06F 18/213* (2023.01)
- *A61B 6/03* (2006.01)

(52) U.S. Cl.
CPC ............... *G06T 2207/20084* (2013.01); *G06T 2207/30004* (2013.01); *G06V 2201/03* (2022.01)

(56) References Cited

OTHER PUBLICATIONS

Fakhfakh, M. et al., "ProgNet: Covid-19 prognosis using recurrent and convolutional neural networks", IEEE, 1-7 (2020).

Tavakolian, M., et al., "A Spatiotemporal Convolutional Neural Network for Automatic Pain Intensity Estimation from Facial Dynamics", Int J Comput Vis 127, 1413-1425 (2019).

\* cited by examiner

SYSTEM AND METHOD FOR DIAGNOSING A DISEASE USING IMAGE CLASSIFICATION

TECHNICAL FIELD

This disclosure relates generally to medical diagnosis, and more particularly relates to system and method for diagnosing a disease using image classification.

BACKGROUND

Generally, conventional mechanisms for diagnosing diseases using image classifications are costly, time consuming, and inaccurate. In many cases, such conventional mechanisms may require precautions to be taken for specific diagnosis. For example, conventional mechanisms may require human intervention with manual validation steps. Further, conventional mechanisms are computationally intensive and may require significant storage and processing power.

Typically, the conventional mechanisms may be based on Convolutional Neural Network (CNN) models that is trained to classify diagnostic images and diagnose diseases based on the diagnostic classes. Such CNN models may be trained to learn class specific features that are distinct among a pre-defined set of diagnostic classes, common features amongst the diagnostic classes, and patterns or features specific to the set of diagnostic classes. Typically, such CNN models include a large number of layers, and, therefore, are computationally intensive. For example, such complex models require a large amount of processing power and memory, specifically while training.

Accordingly, there is a need for system and method with an artificial neural network (ANN) based image classification model for diagnosing disease that is less complex and computationally efficient.

SUMMARY

In an embodiment, a system for diagnosing a disease using image classification is disclosed. The system may include a processor and a memory communicatively coupled to the processor. The memory may be configured to store a temporal convolutional neural network (CNN) model, a plurality of diagnostic images associated with a subject, and processor-executable instructions. The processor-executable instructions, on execution, cause the processor to input a first image of the plurality of diagnostic images captured at a first instance of time to a first pipeline of stacked convolutional layers of the temporal CNN model and a second image of the plurality of diagnostic images captured at a second instance of time to a second pipeline of the stacked convolutional layers of the temporal CNN model. The first pipeline and the second pipeline of the stacked convolutional layers may be configured to extract feature maps from the first image and the second image respectively. The processor instructions further cause the processor to input the feature maps extracted from the first pipeline and the second pipeline to a temporal CNN layer of the temporal CNN model. The temporal CNN layer may be configured to identify relevant feature maps from the feature maps and to generate a concatenated feature map based on the relevant feature maps. The concatenated feature map correspond to a temporal difference between the first image and the second image. The processor instructions further cause the processor to input the concatenated feature map from the temporal CNN layer to fully connected layers of the temporal CNN model. The fully connected layers may be configured to determine an image class corresponding to the second images based on the concatenated feature map. The image class may correspond to at least one of a normal class, an infected class, or an inconclusive class. The processor instructions further cause the processor to diagnose a disease associated with the subject based on the image class.

In another embodiment, a method of diagnosing a disease using image classification is disclosed. The method comprising receiving a plurality of diagnostic images associated with a subject. The plurality of diagnostic images may comprise a first image captured at a first instance of time and a second image captured at a second instance of time. The method further comprising extracting feature maps from the first image and the second image, using a first pipeline of stacked convolutional layers of a temporal convolutional neural network (CNN) model and a second pipeline of the stacked convolutional layers of the temporal CNN model respectively. The method further comprising identifying relevant feature maps from the feature maps, using a temporal CNN layer of the temporal CNN model. The method further comprising generating a concatenated feature map based on the relevant feature maps. The concatenated feature map correspond to a temporal difference between the first image and the second image. The method further comprising determining an image class corresponding to the second image, using a fully connected layers of the temporal CNN model, based on the concatenated feature map. The image class may correspond to at least one of a normal class, an infected class, or an inconclusive class. The method further comprising diagnosing, by the system, a disease associated with the subject based on the image class.

In yet another embodiment, a non-transitory computer-readable storage medium is disclosed. The non-transitory computer-readable storage medium has computer-executable instructions stored thereon for diagnosing a disease using image classification. The computer-executable instructions may cause a computer comprising one or more processors to perform operations comprising receiving a plurality of diagnostic images associated with a subject. The plurality of diagnostic images may comprise a first image captured at a first instance of time and a second image captured at a second instance of time. The operations may further include extracting feature maps from the first image and the second image, using a first pipeline of stacked convolutional layers of a temporal convolutional neural network (CNN) model and a second pipeline of the stacked convolutional layers of the temporal CNN model respectively. The operations may further include identifying relevant feature maps from the feature maps, using a temporal CNN layer of the temporal CNN model, and generating a concatenated feature map based on the relevant feature maps. The concatenated feature map may correspond to a temporal difference between the first image and the second image. The operations may further include determining an image class corresponding to the second image, using a fully connected layers of the temporal CNN model, based on the concatenated feature map. The image class may correspond to at least one of a normal class, an infected class, or an inconclusive class. The operations may further include diagnosing the disease associated with the subject based on the image class.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims. Additional illustrative embodiments are listed below.

The following described implementations may be found in the disclosed system and method for diagnosing a disease using image classification, based on a temporal Convolution Neural Network. Exemplary aspects of the disclosure provide a disease diagnosis system that trains a temporal CNN model to be suitable for real-time inference, while maintaining a balance between a prediction accuracy for image class associated with diagnosing of a disease and compactness of the temporal CNN model. The disclosed disease diagnosis system makes use of temporal differences amongst image classes (such as, a normal class, an infected class and an inconclusive class) from diagnostic images associated with subjects, to reduce a memory usage for processing such images during training time, to reduce the memory usage by not storing a large set of the diagnostic images, and to reduce initial screening time associated with the diagnosis of the disease. In contrast with conventional CNNs, the disclosed system may dynamically diagnose a disease using image classification based on the temporal CNN model while keeping the number of layers of the temporal CNN model required for processing the diagnostic images, computational and model complexity, and memory requirement low.

The temporal CNN model may be trained to learn the temporal differences only amongst the diagnostic images, such that the computations, the number of layers and storage space is reduced. In contrast with conventional CNNs, the number of layers in architecture of the temporal CNN model may be less because features to be learned are less in number as the features are trained only on temporal differences amongst the normal, the infected class and the inconclusive class. Therefore, the memory usage may be drastically reduced for computations during training time. Since, the smaller number of layers saves memory, even high-resolution images can be provided as input for the training of the temporal CNN model as compared to the conventional CNN models.

Figure 1:
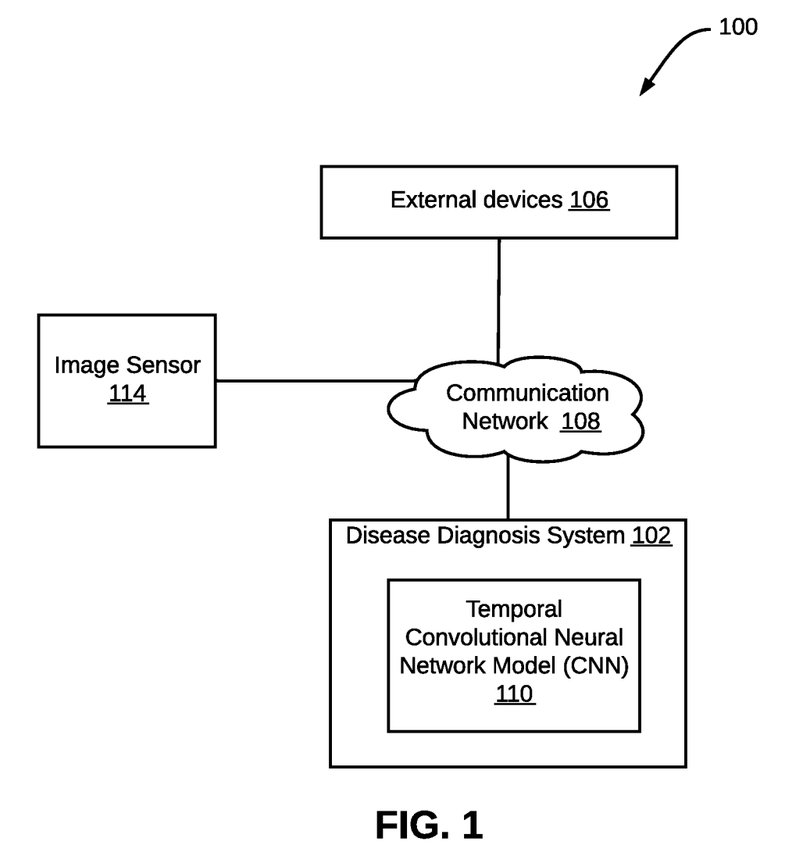
FIG. 1 is a block diagram that illustrates an environment for a disease diagnosis system for diagnosing a disease, in accordance with an embodiment of the disclosure.

FIG. 1 is a block diagram that illustrates an environment for a disease diagnosis system for diagnosing a disease, in accordance with an embodiment of the disclosure. With reference to FIG. 1, there is shown an environment 100. The environment 100 includes a disease diagnosis system 102, an image sensor 104, an external device 106, and a communication network 108. The disease diagnosis system 102 may be communicatively coupled to the image sensor 104 and the external device 106, via the communication network 108. The disease diagnosis system 102 may include a temporal CNN network 110, for example, as part of an application stored in memory of the disease diagnosis system 102.

The disease diagnosis system 102 may include suitable logic, circuitry, interfaces, and/or code that may be configured to train the temporal CNN model 110 for diagnosing a disease. Once trained, the temporal CNN model 110 may determine an image class for diagnosing the disease. Additionally, the temporal CNN model 110, once trained, may be deployable for applications (such as, a diagnostic application) which may take actions or generate real-time or near real-time inferences. By way of example, the disease diagnosis system 102 may be implemented as a plurality of distributed cloud-based resources by use of several technologies that are well known to those skilled in the art. Other examples of implementation of the disease diagnosis system 102 may include, but are not limited to, medical diagnostic equipment, a web/cloud server, an application server, a media server, and a Consumer Electronic (CE) device.

The image sensor 104 may include suitable logic, circuitry, interfaces, and/or code that may be configured to capture a plurality of diagnostic images (also referred as diagnostic images) corresponding to a subject. The diagnostic images may correspond to a sequence of image frames taken at different instances of time associated with the subject. The diagnostic images may be used, for example, to train the temporal CNN model 110, or as an input to the trained temporal CNN model 110 in a test environment (e.g., for benchmarking) or in an application-specific deployment, e.g., applications related to diagnosis of diseases.

By way of an example, and not limitation, the image sensor 104 may have suitable optical instruments, such as lenses and actuators for the lenses, to capture the diagnostic images. Examples of implementation of the image sensor 104 may include, but not limited to, high-definition scanners and cameras (such as, endoscope cameras). Although in FIG. 1, the disease diagnosis system 102 and the image sensor 104 are shown as two separate entities, this disclosure is not so limited. Accordingly, in some embodiments, the entire functionality of the image sensor 104 may be included in the disease diagnosis system 102, without a deviation from scope of the disclosure.

The external device 106 may include suitable logic, circuitry, interfaces, and/or code that may be configured to deploy the temporal CNN model 110, as part of an application engine that may use the output of the temporal CNN model 110 to generate real or near-real time inferences, take decisions, or output prediction results for diagnosis of diseases. The temporal CNN model 110 may be deployed on the external device 106 once the temporal CNN model 110 is trained on the disease diagnosis system 102 to learn the temporal differences among image classes from the captured diagnostic images.

The functionalities of the external device 106 may be implemented in portable devices, such as a high-speed computing device, and/or non-portable devices, such as a server. Examples of the external device 106 may include, but are not limited to, medical diagnosis equipment, a smart phone, a mobile device, or a laptop.

The communication network 108 may include a communication medium through which the disease diagnosis system 102, the image sensor 104, and the external device 106 may communicate with each other. Examples of the communication network 108 may include, but are not limited to, the Internet, a cloud network, a Wireless Fidelity (Wi-Fi) network, a Personal Area Network (PAN), a Local Area Network (LAN), or a Metropolitan Area Network (MAN). Various devices in the environment 100 may be configured to connect to the communication network 108, in accordance with various wired and wireless communication protocols. Examples of such wired and wireless communication protocols may include, but are not limited to, a Transmission Control Protocol and Internet Protocol (TCP/IP), User Datagram Protocol (UDP), Hypertext Transfer Protocol (HTTP), File Transfer Protocol (FTP), Zig Bee, EDGE, IEEE 802.11, light fidelity (Li-Fi), 802.16, IEEE 802.11s, IEEE 802.11g, multi-hop communication, wireless access point (AP), device to device communication, cellular communication protocols, and Bluetooth (BT) communication protocols.

The temporal CNN model 110 may be referred to as a computational network or a system of artificial neurons, where each Neural Network (NN) layer of the temporal CNN model 110 includes artificial neurons as nodes. Outputs of all the nodes in the temporal CNN 110 may be coupled to at least one node of preceding or succeeding NN layer(s) of the temporal CNN model 110. Similarly, inputs of all the nodes in the temporal CNN model 110 may be coupled to at least one node of preceding or succeeding NN layer(s) of the temporal CNN 110. Node(s) in a final layer of the temporal CNN model 110 may receive inputs from at least one previous layer. A number of NN layers and a number of nodes in each NN layer may be determined from hyperparameters of the temporal CNN model 110. Such hyperparameters may be set before or while training the temporal CNN model 110 on a training dataset of diagnostic images.

Each node in the temporal CNN model 110 may correspond to a mathematical function with a set of parameters, tunable while the temporal CNN model 110 is trained. These parameters may include, for example, a weight parameter, a regularization parameter, and the like. Each node may use the mathematical function to compute an output based on one or more inputs from nodes in other layer(s) (e.g., previous layer(s)) of the temporal CNN model 110.

The temporal CNN model 110 may include electronic data, such as, for example, a software program, code of the software program, libraries, applications, scripts, or other logic/instructions for execution by a processing device, such as the disease diagnosis system 102 and the external device 106. Additionally, or alternatively, the temporal CNN model 110 may be implemented using hardware, such as a processor, a microprocessor (e.g., to perform or control performance of one or more operations), a field-programmable gate array (FPGA), or an application-specific integrated circuit (ASIC). In some embodiments, the temporal CNN model 110 may be implemented using a combination of both the hardware and the software program.

In operation, a process may be initialized to train the temporal CNN model 110 on an image classification task, for example, predicting an image class by the image classification from the captured diagnostic images. In training of the temporal CNN model 110, one or more of the set of parameters for each node of the temporal CNN model 110 may be updated.

As part of the process, the disease diagnosis system 102 may input a first image of a plurality of diagnostic images captured at a first instance of time and a second image of the plurality of diagnostic images captured at a second instance of time to the temporal CNN model 110. By way of example, the temporal CNN model 110 may be trained to understand a complex structure from the captured diagnostic images associated with image classes for diagnosing the disease. The disease diagnosis system 102 may be configured to extract a set of features (also referred as feature maps) from the diagnostic images by using two parallel pipelines of stacked convolutional layers of the temporal CNN model 110. The extracted feature maps may correspond to neural activations in the temporal CNN model 110. Further, the disease diagnosis system 102 may be configured to identify relevant feature maps from the extracted feature maps based on generation of relevance values for features in the feature maps of the first image and the second image, using the temporal CNN model 110. The disease diagnosis system 102 may be configured to concatenate feature map for extracting matching features corresponding to predefined image classes using the temporal CNN model 110. The disease diagnosis system 102 may be configured to determine the image class corresponding to the second image using the temporal CNN model 110.

Once trained, the temporal CNN model 110 may be also referred to as the trained temporal CNN model 110, ready to be deployed on suitable devices. After the training, the temporal CNN model 110 may be used to generate image classification results for diagnosing diseases for the diagnostic images that are inputted to the temporal CNN model 110. The disease diagnosis system 102 may deploy the trained temporal CNN model 110 on its own network and for its own applications. Additionally, or alternatively, the disease diagnosis system 102 may deploy the trained temporal CNN 110 on other external devices, such as the external device 106.

Figure 2:
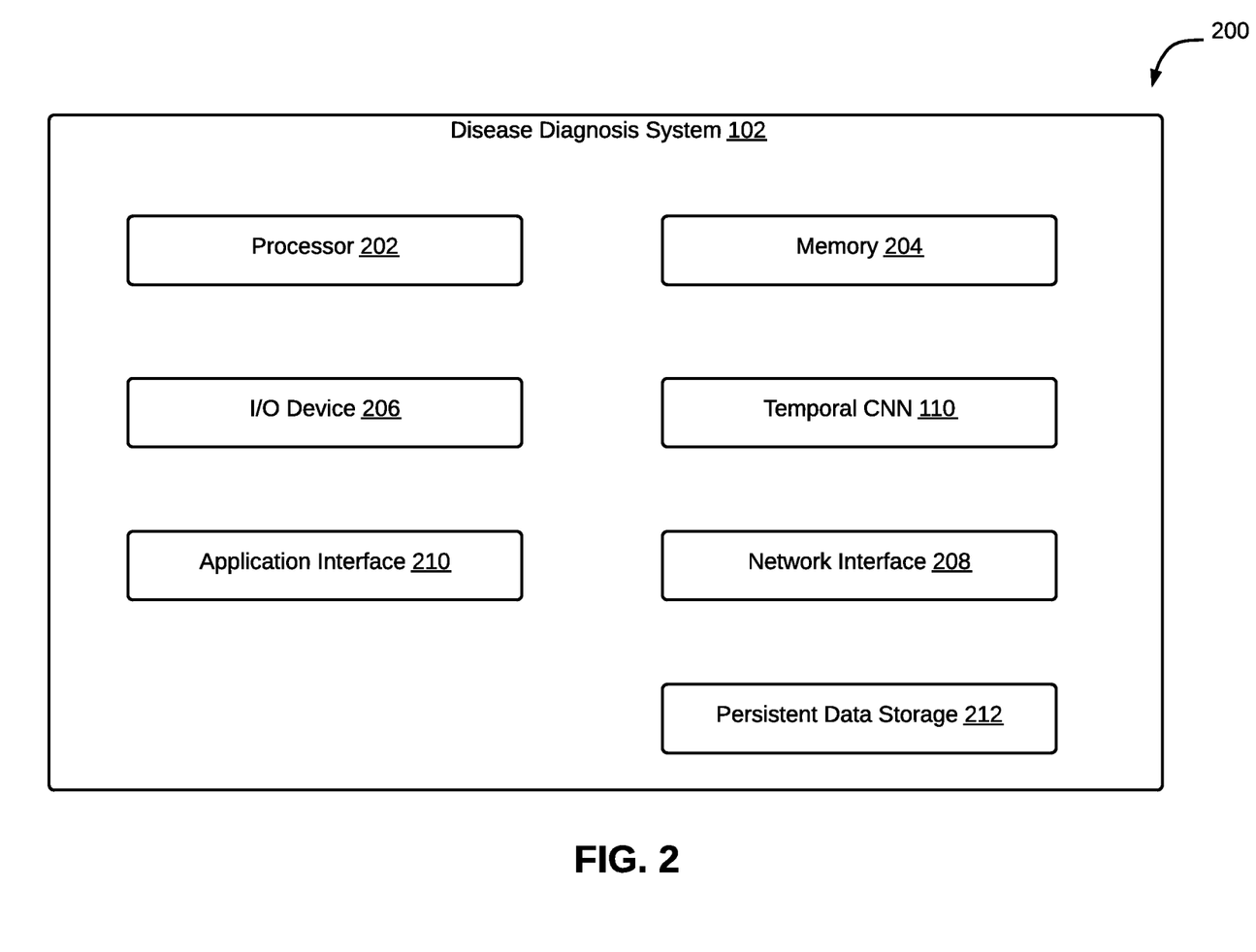
FIG. 2 is a block diagram that illustrates an exemplary disease diagnosis system for diagnosing a disease using a temporal Convolution Neural Network, in accordance with an embodiment of the disclosure.

FIG. 2 is a block diagram of an exemplary disease diagnosis system for diagnosing disease using a temporal CNN model, in accordance with an embodiment of the disclosure. FIG. 2 is explained in conjunction with elements from FIG. 1. FIG. 2 is explained in conjunction with elements from FIG. 1.

With reference to FIG. 2, there is shown a block diagram 200 of the disease diagnosis system 102. The disease diagnosis system 102 may include a processor 202, a memory 204, an input/output (I/O) device 206, a network interface 208, an application interface 210, and a persistent data storage 212. The disease diagnosis system 102 may also include the temporal CNN model 110, as part of, for example, a software application for image-based decisioning in diagnosing diseases. The processor 202 may be communicatively coupled to the memory 204, the I/O device 206, the network interface 208, the application interface 210, and the persistent data storage 212. In one or more embodiments, the disease diagnosis system 102 may also include a provision/functionality to capture images/videos via one or more image sensors, for example, the image sensor 104.

The processor 202 may include suitable logic, circuitry, interfaces, and/or code that may be configured to train the temporal CNN model 110 for multi-class classification task on input diagnostic images. Once trained, the temporal CNN model 110 may be either deployed on other electronic devices (e.g., the external device 106) or on the disease diagnosis system 102 for real time prediction of image class of diagnostic images of a pre-captured images or video feed. The processor 202 may be implemented based on a number of processor technologies, which may be known to one ordinarily skilled in the art. Examples of implementations of the processor 202 may be a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, Artificial Intelligence (AI) accelerator chips, a co-processor, a central processing unit (CPU), and/or a combination thereof.

The memory 204 may include suitable logic, circuitry, and/or interfaces that may be configured to store instructions executable by the processor 202. Additionally, the memory 204 may be configured to store program code of the temporal CNN model 110 and/or the software application that may incorporate the program code of the temporal CNN model 110. Examples of implementation of the memory 204 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The I/O device 206 may include suitable logic, circuitry, and/or interfaces that may be configured to act as an I/O interface between a user and the disease diagnosis system 102. The user may include a general practitioner who operates the disease diagnosis system 102 for performing a screening test of a patient, or a patient who undergoes a screening test for disease identification. The I/O device 206 may include various input and output devices, which may be configured to communicate with different operational components of the disease diagnosis system 102. Examples of the I/O device 206 may include, but are not limited to, a touch screen, a keyboard, a mouse, a joystick, a microphone, and a display screen.

The network interface 208 may include suitable logic, circuitry, interfaces, and/or code that may be configured to facilitate different components of the disease diagnosis system 102 to communicate with other devices, such as the external device 106, in the environment 100, via the communication network 108. The network interface 208 may be configured to implement known technologies to support wired or wireless communication. Components of the network interface 208 may include, but are not limited to an antenna, a radio frequency (RF) transceiver, one or more amplifiers, a tuner, one or more oscillators, a digital signal processor, a coder-decoder (CODEC) chipset, an identity module, and/or a local buffer.

The network interface 208 may be configured to communicate via offline and online wireless communication with networks, such as the Internet, an Intranet, and/or a wireless network, such as a cellular telephone network, a wireless local area network (WLAN), personal area network, and/or a metropolitan area network (MAN). The wireless communication may use any of a plurality of communication standards, protocols and technologies, such as Global System for Mobile Communications (GSM), Enhanced Data GSM Environment (EDGE), wideband code division multiple access (W-CDMA), code division multiple access (CDMA), LTE, time division multiple access (TDMA), Bluetooth, Wireless Fidelity (Wi-Fi) (such as IEEE 802.11, IEEE 802.11b, IEEE 802.11g, IEEE 802.11n, and/or any other IEEE 802.11 protocol), voice over Internet Protocol (VoIP), Wi-MAX, Internet-of-Things (IoT) technology, Machine-Type-Communication (MTC) technology, a protocol for email, instant messaging, and/or Short Message Service (SMS).

The application interface 210 may be configured as a medium for the user to interact with the disease diagnosis system 102. The application interface 210 may be configured to have a dynamic interface that may change in accordance with preferences set by the user and configuration of the disease diagnosis system 102. In some embodiments, the application interface 210 may correspond to a user interface of one or more applications installed on the disease diagnosis system 102.

The persistent data storage 212 may include suitable logic, circuitry, and/or interfaces that may be configured to store program instructions executable by the processor 202, operating systems, and/or application-specific information, such as logs and application-specific databases. The persistent data storage 212 may include a computer-readable storage media for carrying or having computer-executable instructions or data structures stored thereon. Such computer-readable storage media may include any available media that may be accessed by a general-purpose or special-purpose computer, such as the processor 202.

By way of example, and not limitation, such computer-readable storage media may include tangible or non-transitory computer-readable storage media including, but not limited to, Compact Disc Read-Only Memory (CD-ROM) or other optical disk storage, magnetic disk storage or other magnetic storage devices (e.g., Hard-Disk Drive (HDD)), flash memory devices (e.g., Solid State Drive (SSD), Secure Digital (SD) card, other solid state memory devices), or any other storage medium which may be used to carry or store particular program code in the form of computer-executable instructions or data structures and which may be accessed by a general-purpose or special-purpose computer. Combinations of the above may also be included within the scope of computer-readable storage media.

Computer-executable instructions may include, for example, instructions and data configured to cause the processor 202 to perform a certain operation or a set of operations associated with the disease diagnosis system 102. The functions or operations executed by the disease diagnosis system 102, as described in FIG. 1, may be performed by the processor 202. In accordance with an embodiment, additionally, or alternatively, the operations of the processor 202 are performed by various modules that are described in detail, for example, in FIG. 4.

Figure 3:
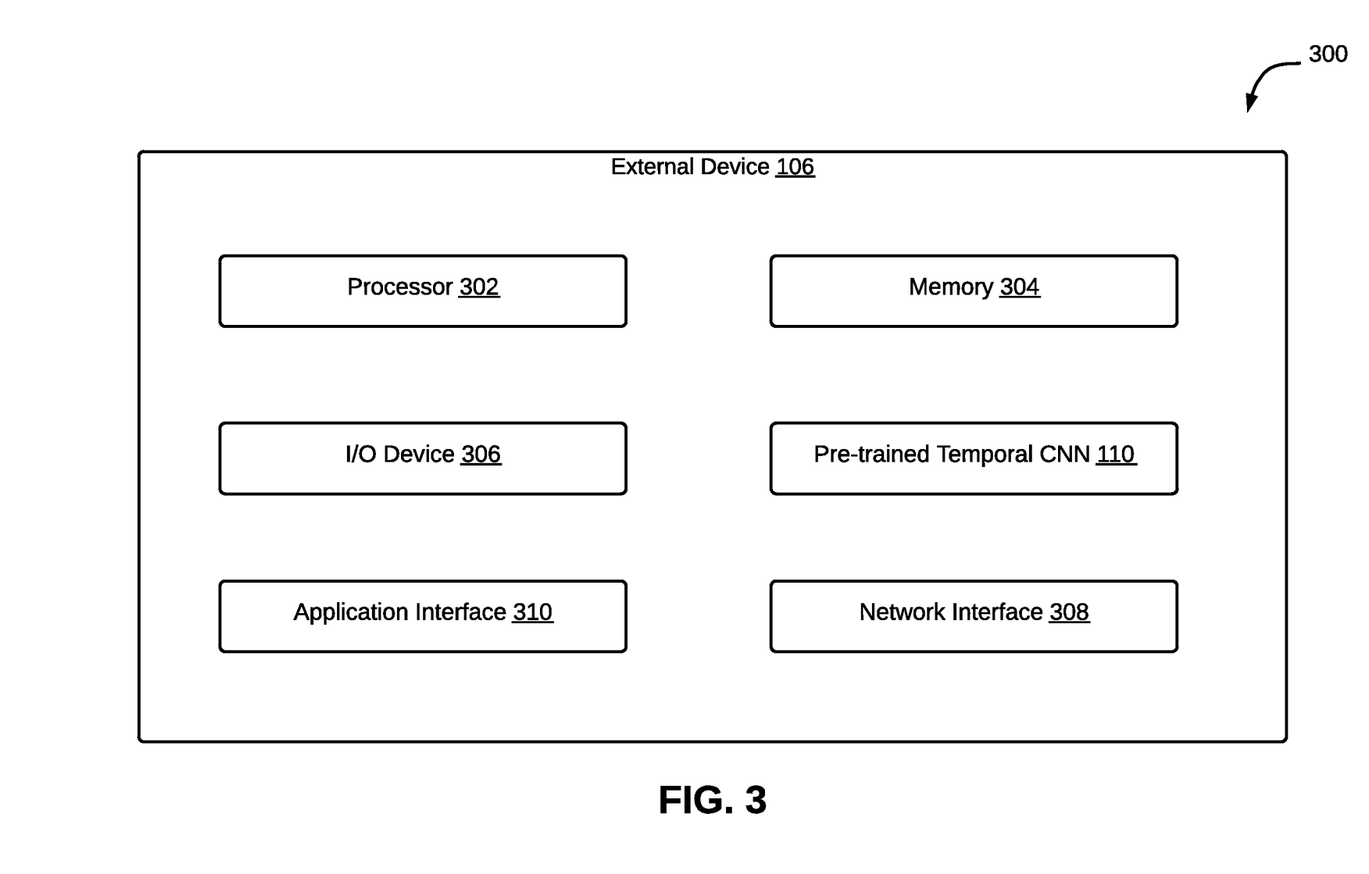
FIG. 3 is a block diagram that illustrates an exemplary external device for diagnosing a disease using a pre-trained temporal Convolution Neural Network, in accordance with an embodiment of the disclosure.

FIG. 3 illustrates a block diagram of an exemplary external device for diagnosing disease using a pre-trained temporal Convolution Neural Network model, in accordance with an embodiment of the disclosure. FIG. 3 is explained in conjunction with elements from FIG. 1 and FIG. 2.

With reference to FIG. 3, there is shown a block diagram 300 of the external device 106. The external device 106 may include a processor 302, a memory 304, an I/O device 306, a network interface 308, and an application interface 310. The temporal CNN model 110, once trained, may be deployed on the external device 106, as part of another software application, for example, for diagnosing the disease using image classification. The processor 302 may be communicatively coupled to the memory 304, the I/O device 306, the network interface 308, and the application interface 310. In at least one embodiment, the external device 106 may also include a provision/functionality to capture diagnostic images via one or more image sensors, for example, the image sensor 104.

The processor 302 may include suitable logic, circuitry, interfaces, and/or code that may be configured to implement the temporal CNN model 110 after the temporal CNN model 110 is trained for the multi-class classification task on inputted diagnostic images. The processor 302 may be implemented based on a number of processor technologies, which may be known to one ordinarily skilled in the art. An exemplary implementation of the processor 302 may be processor(s) of medical diagnosis equipment. Further example implementations of the processor 302 may be a Graphics Processing Unit (GPU), a Reduced Instruction Set Computing (RISC) processor, an Application-Specific Integrated Circuit (ASIC) processor, a Complex Instruction Set Computing (CISC) processor, a microcontroller, Artificial Intelligence (AI) accelerator chip(s), a co-processor, a central processing unit (CPU), and/or a combination thereof.

The memory 304 may include suitable logic, circuitry, and/or interfaces that may be configured to store instructions executable by the processor 302. Additionally, the memory 304 may be configured to store the temporal CNN model 110 pre-trained to dynamically determine image class for the captured diagnostic images for accurate disease diagnosis based on the temporal CNN model 110. The memory 304 may also store a program code of the temporal CNN model 110 and/or the software application that may incorporate the program code of the temporal CNN model 110. Examples of implementation of the memory 304 may include, but are not limited to, Random Access Memory (RAM), Read Only Memory (ROM), Electrically Erasable Programmable Read-Only Memory (EEPROM), Hard Disk Drive (HDD), a Solid-State Drive (SSD), a CPU cache, and/or a Secure Digital (SD) card.

The I/O device 306 may include suitable logic, circuitry, and/or interfaces that may be configured to act as an I/O interface between a user and the external device 106. The I/O device 306 may include various input and output devices, which may be configured to communicate with different operational components of the external device 106. Examples of the I/O device 306 may include, but are not limited to, a touch screen, a keyboard, a mouse, a joystick, a microphone, and a display screen.

The network interface 308 may include suitable logic, circuitry, interfaces, and/or code that may be configured to facilitate different components of the external device 106 to communicate with other devices in the environment 100, via the communication network 108. The network interface 308 may be configured to implement known technologies to support wired or wireless communication. Components of the network interface 308 may include, but are not limited to an antenna, a radio frequency (RF) transceiver, one or more amplifiers, a tuner, one or more oscillators, a digital signal processor, a coder-decoder (CODEC) chipset, an identity module, and/or a local buffer. The network interface 308 may be configured to communicate via offline and online wireless communication with networks, such as the Internet, an Intranet, and/or a wireless network, such as a cellular telephone network, a wireless local area network (WLAN), personal area network, and/or a metropolitan area network (MAN).

The application interface 310 may be configured as a medium for the user to interact with the external device 106. The application interface 310 may be configured to have a dynamic interface that may change in accordance with preferences set by the user and configuration of the external device 106. In some embodiments, the application interface 310 may correspond to a user interface of one or more applications installed on the external device 106. For example, the application interface may be displayed on a high-definition scanner unit and may allow a user to visualize information processed by the external device 106. The functions or operations executed by the external device 106, as described in FIG. 1, may be performed by the processor 302.

Figure 4:
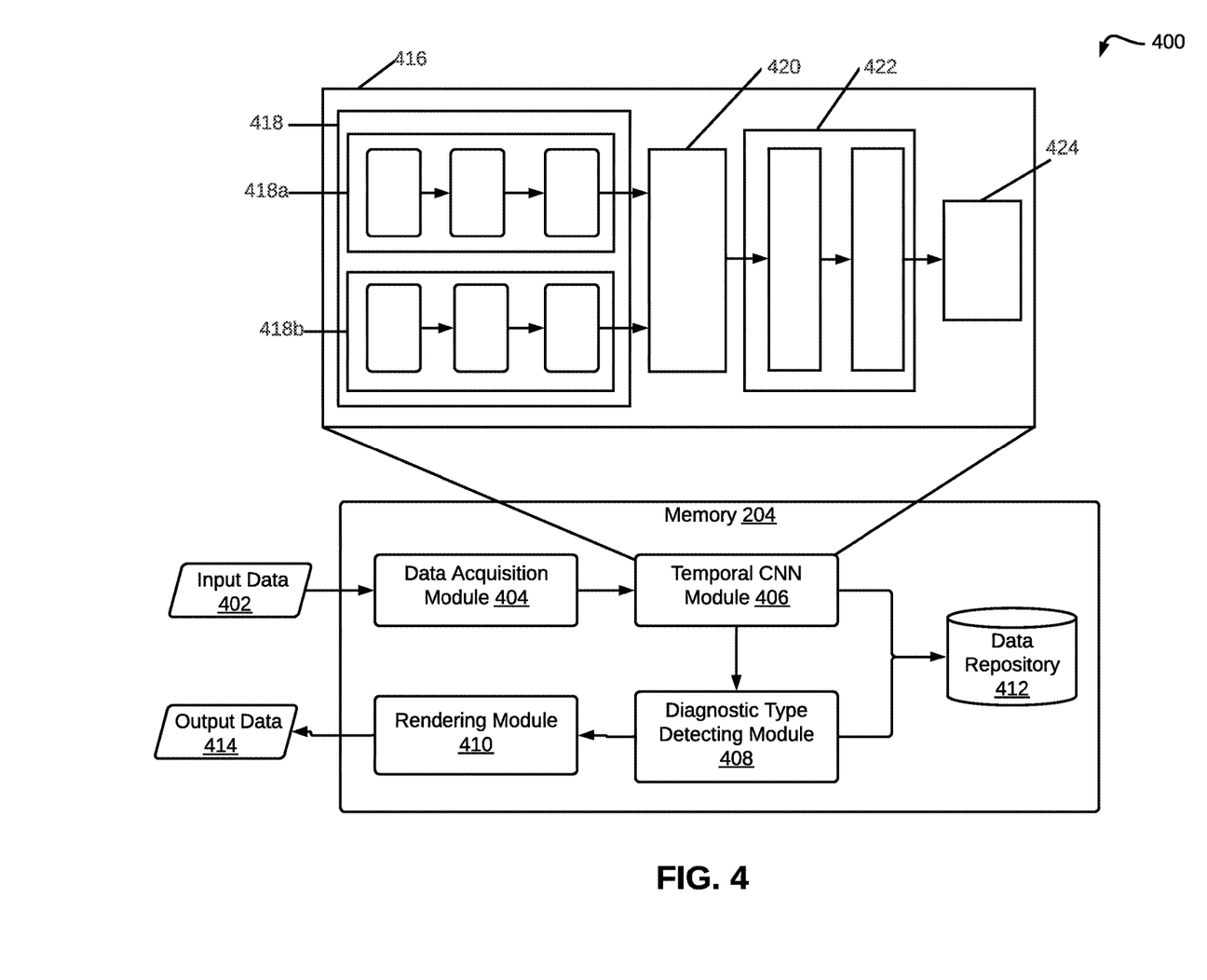
FIG. 4 is a functional block diagram that illustrates various modules of a disease diagnosis system for diagnosing a disease, in accordance with an embodiment of the disclosure.

FIG. 4 is a functional block diagram 400 that illustrates various modules of a disease diagnosis system for diagnosing a disease using image classification, in accordance with an embodiment of the disclosure. FIG. 4 is explained in conjunction with elements from FIG. 1, FIG. 2, and FIG. 3.

With reference to FIG. 4, there is shown image data 402, a data acquisition module 404, a temporal CNN module 406, a diagnostic prediction module 408, a rendering module 410, a data repository 412, and output data 414. Further, there is shown in the temporal CNN module 406, a temporal CNN model 416 with an input layer 418 of stacked convolutional layers having a first pipeline 418a and a second pipeline 418b, an intermediate layer 420 (hereinafter referred as a temporal CNN layer 420), fully connected layers 422 and a SoftMax layer 424. The temporal CNN model 416 may correspond to the temporal CNN model 110 of FIG. 1 and modelled on a deep neural network architecture with multiple stages. Details of functionality of the aforementioned layers/blocks of the temporal CNN model 416 are also covered in detail, for example, in FIG. 5.

Referring to FIG. 4, the data acquisition module 404 of the disease diagnosis system 102 may be configured to receive the image data 402. The image data 402 may be received from the image sensor 104. In accordance with an embodiment, the image data 402 may correspond to a plurality of diagnostic images associated with a subject. In accordance with an embodiment, the data acquisition module 404 may be configured to process the image data based on image reconstruction techniques. The examples for the image reconstruction techniques may include, but not limited to, a back projection technique, an inverse Fourier transform technique, and a sparse reconstruction technique.

In accordance with an embodiment, a first image of the plurality of diagnostic images may be captured at a first instance of time by the image sensor 104. In accordance with an embodiment, the first image of the plurality of diagnostic images may correspond to a normal image. The normal image may belong to a normal class (from the image class) with no disease associated. In accordance with another embodiment, a second image of the plurality of diagnostic images may be captured at a second instance of time by the image sensor 104. For example, the first image and the second image are captured ten minutes apart. In accordance with an embodiment, the second image of the plurality of diagnostic images may correspond to a decision image.

In accordance with an embodiment, the decision image may belong to a diagnostic class associated with a disease or inconclusive class. In certain embodiments, one or more decision images may be captured by the image sensor 104 and thereby, the decision images may be labelled as a first decision image, a second decision image and so forth.

In accordance with an embodiment, the plurality of diagnostic images may be captured at a time interval that is specific to the type of dataset being used. For example, in case of diagnosis of a respiratory disease, identification of the infection may be based on the existence of virus in a respiratory track of a human body. In such a scenario, two diagnostic images (for example, the first image and the second image) of the respiratory track for the patient may be obtained within a time interval of 10 minutes. In accordance with an embodiment, the first image may be captured when the respiratory track is clean. In accordance with an embodiment, the second image may be captured after 10 minutes of capturing of the first image. The first image may correspond to a sample/normal image and the second image may correspond to the decision image.

The data acquisition module 404 may transmit the first image of the plurality of diagnostic images and the second image of the plurality of diagnostic images to the first pipeline 418a and the second pipeline 418b of the temporal CNN model 416 in the temporal CNN module 406 respectively.

In accordance with an embodiment, the first pipeline 418a of the stacked convolutional layers 418 may correspond to a normal pipeline that receives the first image (normal image) as an input. In accordance with an embodiment, the second pipeline 418b of the stacked convolutional layers 418 may correspond to a decision pipeline that receives the second image (decision image) as an input.

After receiving the first image and the second image of the plurality of diagnostic images, the stacked convolutional layers 418 of the temporal CNN model 416 in the temporal CNN module 406 may be configured to extract feature maps from the first image and the second image of the plurality of diagnostic images. The temporal CNN layer 420 of the temporal CNN model 416 in the temporal CNN module 406 may be configured to identify relevant feature maps extracted from the feature maps of the first image and the second image. The relevant feature maps may indicate a temporal difference among image classes from the first image and the second image.

The relevant feature maps for the first image and the second image may be identified based on relevance values generated corresponding to the feature maps. The relevance values may be generated using a Layer Wise Relevance Propagation (LRP) algorithm. In accordance with an embodiment, the LRP may be computed by back propagating relevance of predicted classes through a plurality of layers of models (such as, the temporal CNN model 416) from output to input. A relative relevance at any layer of the temporal CNN model 416 may be computed by appropriately distributing the relevance among different neurons in the temporal CNN model 416. For example, the activation of the neuron at a specific layer of the temporal CNN model 416 is 10 and sum of activation of all neurons in that specific layer is 100. Therefore, the relevance of the neuron is 10/100=0.1. The relevance of the neuron is given by the equation (1):

$$\text{Relevance of neuron} = \text{activation at specific layer/sum of activation in specific layer} \quad \text{Equation (1)}$$

The feature maps are output of intermediate layers of CNN models (such as, the temporal CNN model 416). Each feature map at any layer may indicate the features learned by that layer. Further, the temporal CNN module 406 may be configured to identify highly relevant activation feature maps (also referred to as relevant feature maps) from the feature maps based on the relevant features (i.e., activated neurons) and discard remaining features in the feature maps.

The identification of the highly relevant feature maps may be based on a number of times a feature map is detected to be highly activated while processing an entire training data set of the diagnostic images. For example, from a 100 training samples in a training dataset, when the feature map is highly activated in 80 samples, then the feature map may correspond to a pure feature map.

During evaluation, when the highly relevant feature maps may correspond to one of the elements in a set of pure feature maps, then such highly relevant feature maps may be retained. On selection of a threshold number of the highly relevant activation feature maps from the first pipeline 418a and the second pipeline 418b, the temporal CNN module 406 may be configured to sort the highly relevant activation feature maps and concatenate the highly relevant feature maps to form a union of the highly relevant activation feature maps. The union of the highly relevant activation feature maps may correspond to concatenated feature map. In accordance with an embodiment, the threshold number may be configured during training of the temporal CNN model 416. In another embodiment, the threshold number may be configured in real time or near real time.

The temporal CNN module 406 may be configured to pass the concatenated feature map to the fully connected layers 422 of the temporal CNN model 416 for further processing. On receiving the concatenated feature map after processing from the fully connected layers 422, the SoftMax layer 424 in the temporal CNN module 406 may be used by the temporal CNN module 406 to provide a final prediction. A SoftMax function of the SoftMax layer 424 may take a vector of "m" real values, which can be a positive value, a negative value or a zero value. Further, the SoftMax function may turn them into a vector "m" of real values that is summed up to one. The SoftMax function may output values that are in the range "0" and "1" and may be interpreted as probabilities. The SoftMax layer 424 may be used by the temporal CNN module 406 to predict whether the class output is a "normal" class, "an infected" class or "an inconclusive" class. In accordance with an embodiment, the SoftMax layer 424 may be used by the temporal CNN module 406 to predict the class output as "unknown" class.

Further, the temporal CNN module 406 may be configured to transmit the second image (decision image) of the plurality of diagnostic images to the diagnostic prediction module 408 to detect an accurate image class to which the second image belongs. Further, the temporal CNN module 406 may be configured to transmit prediction class outputs with class labels and probabilities to the data repository 412.

The diagnostic prediction module 408 may be configured to receive the second image (decision image) from the temporal CNN module 406. The diagnostic prediction module 408 may be configured to predict a type of image class associated with the second image (decision image) based on the prediction of the infected class by the temporal CNN module 406. The diagnostic prediction module 408 may use a CNN classifier to predict the type of infection in the second image. For example, the temporal CNN module 406 has predicted the 'infected' class as pneumonia then, the diagnostic prediction module 408 predicts the type of pneumonia. In accordance with an embodiment, the class output labelled as "unknown" may be used for classification of all the decision images (such as, the second image) in which new patterns or unknown patterns/clusters are identified.

The diagnostic prediction module 408 may be further configured to train the diagnostic images with high accuracy using a CNN model, such as, but not limited to, Inception Net and ResNet. The diagnostic prediction module 408 may train based on transfer learning algorithm for decision images with high accuracy. Further, the diagnostic prediction module 408 may be configured to transmit predicted information for infected class to the data repository 412. Further, the diagnostic prediction module 408 may be configured to transmit the predicted information for infected class to the rendering module 410.

The rendering module 410 may be configured to receive the predicted information for the infected class from the diagnostic prediction module 408. Further, the rendering module 410 may be configured to render the output data 414 associated with the predicted information to the user. The user may correspond to a patient or a medical practitioner. The rendering module 410 may be configured to fetch information from the data repository 412 associated with the predicted information to render the output data 414 on a user device. In accordance with an embodiment, the output data may be rendered as a diagnosis report on the user device. The diagnosis report may include the image class and one of: the disease when the image class may correspond to the infected class, and a recommendation when the image class may correspond to the inconclusive class.

The data repository 412 may be configured to receive predicted image class outputs with class labels and probabilities from the temporal CNN module 406. Further, the data repository 412 may be configured to receive the predicted information for infected class from the diagnostic prediction module 408. Further, the data repository 412 may be configured to store information that is required for processing in run time. Such information may include diagnostic images, predicted classes, dataset of training images, dataset of test images, and diagnosis reports. The data repository 412 may correspond to a high-speed data repository, such as, but not limited to, Redis, and NoSQL.

Figure 5:
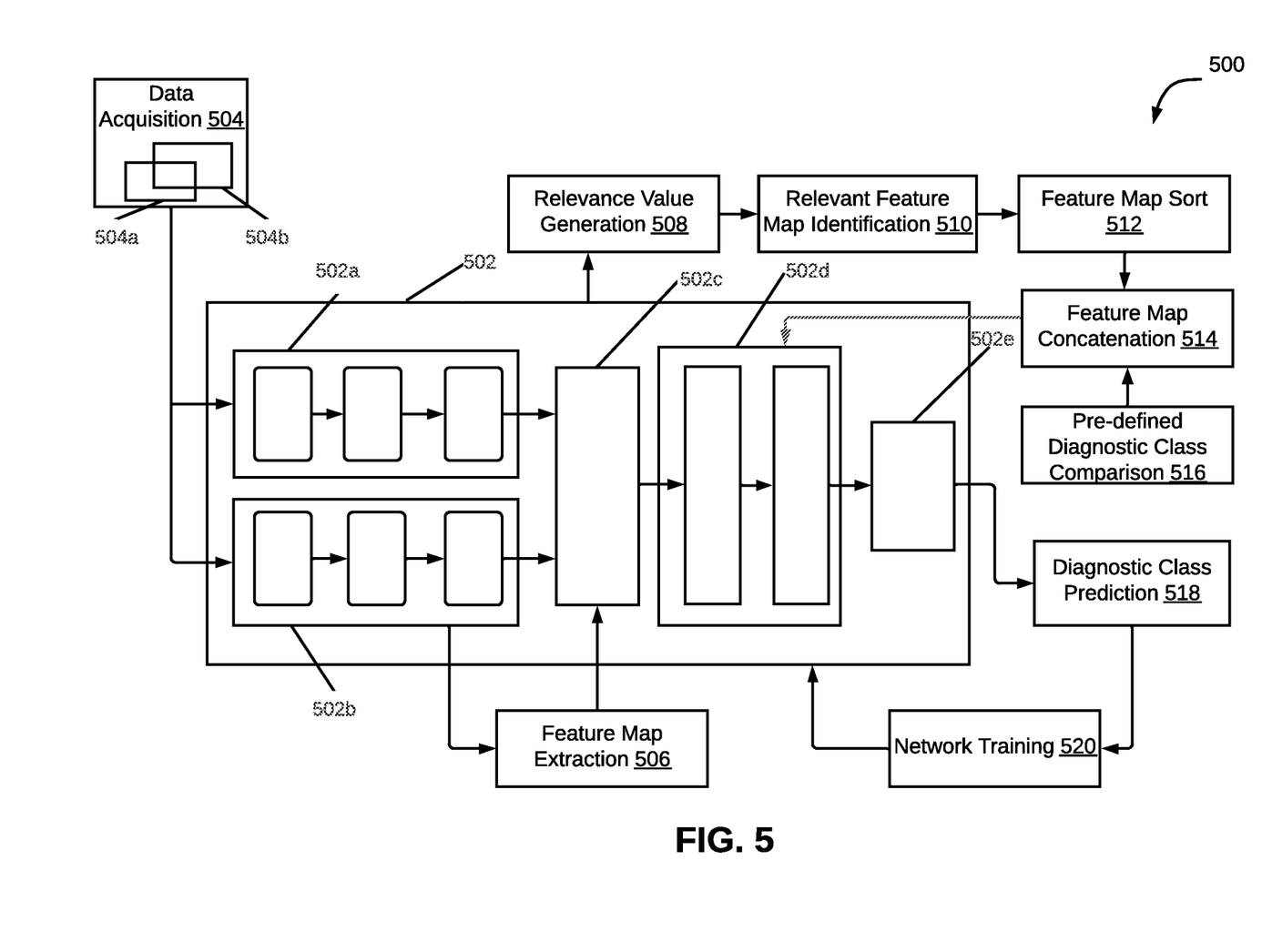
FIG. 5 is a diagram that illustrates exemplary operations for training of a temporal CNN model for a prediction of image class to diagnose a disease, in accordance with an embodiment of the disclosure.

FIG. 5 is a diagram that illustrates exemplary operations for training of a temporal CNN model for a prediction of image class to diagnose a disease, in accordance with an embodiment of the disclosure. FIG. 5 is explained in conjunction with elements from FIG. 1 to FIG. 4. With reference to FIG. 5, there is shown a diagram 500 that illustrates a set of operations for training of a temporal CNN model 502 for prediction of an image class to diagnose a disease, as described herein.

The temporal CNN model 502 may correspond to the temporal CNN 102 of FIG. 1 and may be, for example, modelled on a deep neural network architecture with multiple stages.

At 504, a data acquisition operation may be performed. In the data acquisition operation, the data acquisition module 404 may acquire a training dataset which may include a sequence of diagnostic images (also referred as training images). An example of the training dataset may be used to train deep neural networks for identifying temporal differences among image classes from the diagnostic images, and to benchmark relative performance and accuracy of the trained deep neural networks. As shown, for example, the sequence of diagnostic images in the training dataset includes a first image 504a and a second image 504b.

The training images may correspond to a set of subjects. In accordance with an embodiment, the training images may include, but not limited to, X-ray images, Computed Tomography (CT) scan images, any medical images, Positron emission tomography (PET) scan, microscopy images, and temporally differing images. The training images may be received to generate a model (for example, the temporal CNN model 502). Such temporal CNN model 502 may be trained to predict the image class for diagnostic images corresponding to a subject (patient).

In accordance with an embodiment, the data acquisition module 404 may receive the sequence of diagnostic images as signals from the image sensor 104. In accordance with an embodiment, a signal may correspond to a skin image. The signal may further correspond to a 1-dimensional signal or a 2-dimensional signal. The 1-dimensional signal may be converted into the 2-dimensional signal by using techniques, such as, but not limited to, Short-term Fourier Transform, Wavelet Transform, and Mel Spectrogram. The data acquisition module 404 may perform further processing on the converted 2-dimensional signal. The processing may include measures for degree of dehydration, PPG signal/thumb image excited with a light source to measure heart rate variation, pulse rate variation, redness in face to measure fluctuations in body temperature, variations in vibrations of lungs captured with chest image to screen pneumonia, 1-dimensional spot signal to measure variations in oxygen level for diagnosis, or the like.

In accordance with an embodiment, the sequence of diagnostic images may correspond to a good optical quality images captured with 140 times magnification and imaging resolution of 2 microns that may enable minute patterns to be captured in the sequence of diagnostic images. In accordance with an embodiment, a training image corresponding to a normal image class may be categorized as a normal image and a training image corresponding to the decision class may be categorized as a decision image-1, a decision image-2, and so forth. The data acquisition module 404 may pre-process the sequence of diagnostic images, such as the training images 504a and 504b using cropping and other image operations to make them suitable for processing by the temporal CNN model 502. The data acquisition module 404 may be further configured to transmit the sequence of diagnostic images to the temporal CNN model 502.

At 506, a feature map extraction operation may be performed. In the feature map extraction operation, the temporal CNN module 406 may extract the feature maps from each of the training images (such as the training image 504a and the training image 504b). The extracted feature map for each of the training images (such as the training image 504a and the training image 504b) are generated simultaneously from the first pipeline 502a and the second pipeline 502b of stacked convolutional layers. The first pipeline 502a may receive normal image as input training image (such as the training image 504a) and the second pipeline 502b may receive decision image as the input training image (such as the training image 504a).

The extracted feature map(s) may correspond to machine-readable feature maps that are reflected as neural activations. In accordance with an embodiment, one of the input training images (such as the training image 504a) may correspond to a predefined class and another input training image (such as the training image 504b) corresponds to a binary class. The binary class may either correspond to a normal class or an infected class. The extracted feature map may correspond to, but not limited to, contours (edges) of the training images, intensity variations, image orientation and degree of tilt.

Further, the extracted feature maps from the first pipeline 502a and the second pipeline 502b of the stacked convolutional layers may be transmitted to the temporal convolutional layer 502c of the temporal CNN model 502. In accordance with an embodiment, a number of convolutional layers in the temporal CNN model 502 are configured in such a way that the best performance is obtained from generation of the temporal CNN model 502.

The temporal convolutional layer 502c may be configured to receive feature maps of the stacked convolution layers from the first pipeline (or normal pipeline) 502a and the second pipeline (or decision pipeline) 502b. The feature maps may depict the features learned from the normal images (such as the training image 504a) and the decision images (such as the training image 504b). The features, in the feature maps, may be learnt independently using the first pipeline 502a and the second pipeline 502b of the stacked convolutional layers. Hence, the first pipeline (normal pipeline) 502a may learn the features of patterns or clusters of normal image class only in the training images. Further, the second pipeline (decision pipeline) 502b may learn the features of patterns or clusters of all the decision classes that may be one of an infected class, a normal class or an inconclusive class. For example, for nCovid-19 diagnosis, the decision classes are either non-nCovid-19 class or nCovid-19 class.

At 508, a relevance value generation operation may be performed. In the relevance value generation operation, the temporal CNN module 406 may generate relevance values from the temporal convolutional layer 502c of the temporal CNN model 502. In accordance with an embodiment, the relevance values may be generated based on a Layer Wise Relevance Propagation (LRP) technique.

At 510, a relevant feature map identification operation may be performed. In the relevant feature map identification operation, the temporal CNN module 406 may identify the relevant feature maps from the temporal convolutional layer 502c of the temporal CNN model 502, based on the generated relevance values for the feature maps above a threshold value. Alternatively, or additionally, the temporal convolutional layer 502c may be configured to identify irrelevant feature maps based on the generated relevance values for the feature maps below the threshold value. Such feature maps may be discarded by the temporal convolutional layer 502c. Depending on the observation during training phase of the temporal CNN model 502, the threshold value may be set for the number of feature maps that needs to be considered for processing.

At 512, a relevant feature map sort operation may be performed. In the relevant feature map sort operation, the temporal CNN module 406 may sort the relevant feature maps from the temporal convolutional layer 502c of the temporal CNN model 502, based on the relevance values when the threshold number of highly relevant feature maps are selected from the first pipelines 502a and the second pipeline 502b.

At 514, a feature map concatenation operation may be performed. In the feature map concatenation operation, the temporal CNN module 406 may concatenate the relevant feature map from the temporal convolutional layer 502c of the temporal CNN model 502, based on sorting of the relevant feature maps. In accordance with an embodiment, the concatenated feature map may aid in processing or reading the feature maps accurately. The concatenated feature map may also facilitate in performing inferencing of input images as to which image class the input images belong (normal, inconclusive or infected) in a better way. Further, the concatenated feature map determined in the decision image that may bring in a temporal difference to the two diagnostic classes are isolated and used for inferencing. For example, the temporal difference may be highlighted in the length of a certain item, and clustering, as evident from the specific neural activations. Further, the temporal convolutional layer 502c may be configured to map the concatenated feature maps to a corresponding predefined diagnostic class 516 stored in the data repository 412. In accordance with an embodiment, such feature maps may be stored in the data repository 412 for utilization in real time or near real time.

Further, the concatenated feature maps may be fed from the temporal convolutional layer 502c to fully connected (FC) layers 502d. In accordance with an embodiment, the FC layers 502d may be used by the temporal CNN module 406 to predict a diagnostic class as one of a normal class, an infected class or an inconclusive class. In accordance with another embodiment, the FC layers 502d may be configured to transmit the concatenated feature map to a SoftMax layer 502e.

At 518, a diagnostic (image) class prediction operation may be performed. In the diagnostic class prediction operation, the SoftMax layer 502e may predict the diagnostic class/image class corresponding to the input image (decision image) for categorization. The concatenated feature map may be used by the temporal CNN model 502 of the temporal CNN module 406 to detect or predict the image class for the second training image 504b.

At 520, a network training operation may be performed. In the network training operation, the temporal CNN module 406 may train the temporal CNN model 502 for the prediction of the image class based on a temporal difference amongst the sequence of diagnostic images (such as, the training image 504a and the training image 504b).

In contrast to conventional CNN models, the temporal CNN model 502, once trained, may offer a reduced computational complexity, and a reduced parameter size. In contrast, the conventional CNN models have a higher computation complexity, larger parameter size due to larger number of computations in the training. Once trained, the temporal CNN model 502 may be suitable for understanding of complex diagnostic images to produce real time inferences and make suitable decisions.

Although, in FIG. 5, discrete operations from 504 to 520 are described, the disclosure may not be so limited. Accordingly, in certain embodiments, such discrete operations may be further divided into additional operations, combined into fewer operations, or eliminated, depending on the particular implementation without detracting from the essence of the disclosed embodiments. After the training, the trained temporal CNN model 502 may be used to generate prediction results to diagnose diseases for diagnostic images as input to the trained temporal CNN model 502.

Figure 6:
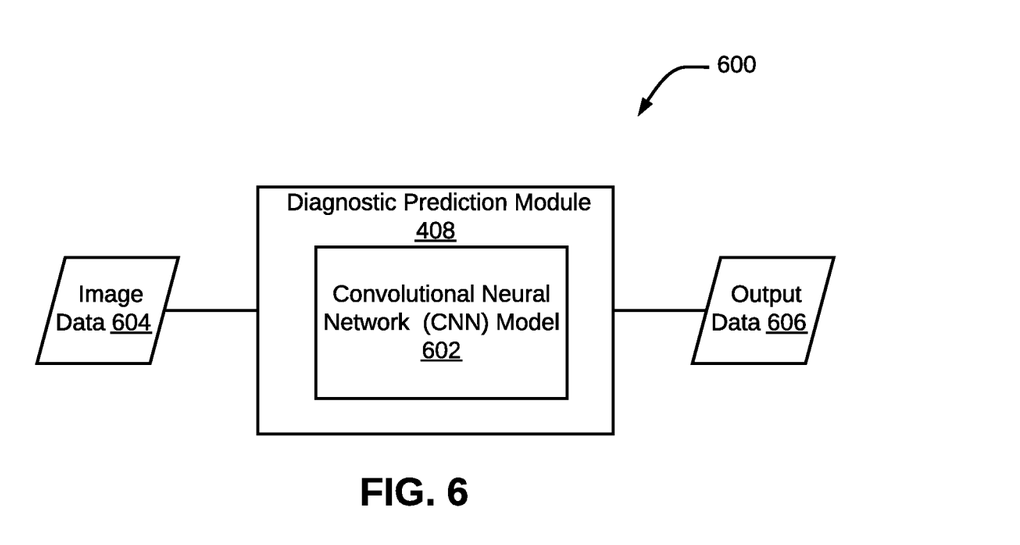
FIG. 6 is a block diagram that illustrates a Convolutional Neural Network (CNN) used by a diagnostic prediction module to predict a type of infection for diagnostic images, in accordance with an embodiment of the disclosure.

FIG. 6 is a block diagram that illustrates a Convolutional Neural Network (CNN) used by a diagnostic prediction module of a disease diagnosis system to predict a type of infection for diagnostic images, in accordance with an embodiment of the disclosure. With reference to FIG. 6, there is shown a block diagram 600 with a CNN 602, input data 604 and output data 606.

As described in FIG. 5, the predicted diagnostic class (image class) may be transmitted from the temporal CNN module 406 to the diagnostic prediction module 408 for detecting a type of the diagnostic class, based on the predicted diagnostic class. The predicted diagnostic class may be one of a normal class, an infected class and an inconclusive class. With reference to FIG. 6, based on the predicted diagnostic class not corresponding to the normal class, the diagnostic prediction module 408 may use the CNN model 602 (such as, Inception Net and ResNet) to detect the type of the diagnostic class. The CNN model 602 may be trained with input data 604 that corresponds to decision images 604 using transfer learning algorithms to detect the type of the diagnostic class.

In accordance with an embodiment, a first set of convolution layers in the CNN model 602 may be frozen. In accordance with an embodiment, last two or three convolutional layers and rest of architecture for the CNN model 602 may be trained as part of the transfer learning algorithm. The transfer learning algorithm may be used to focus on storing knowledge gained while solving one problem and applying to a different but related problem. The trained CNN model 602 that is a part of the diagnostic prediction module 408 may be used in real time or near real time for prediction of the type of infection by the diagnostic prediction module 408. Further, a class label called "unknown" may be used to classify the diagnostic images 604 in which new or unknown patters or clusters are identified. In accordance with an embodiment, when the prediction may be unknown, the decision image 604 may be provided for further analysis to experts (such as, a medical practitioner or a diagnostic imaging expert) to detect new patterns and clusters.

Figure 7:
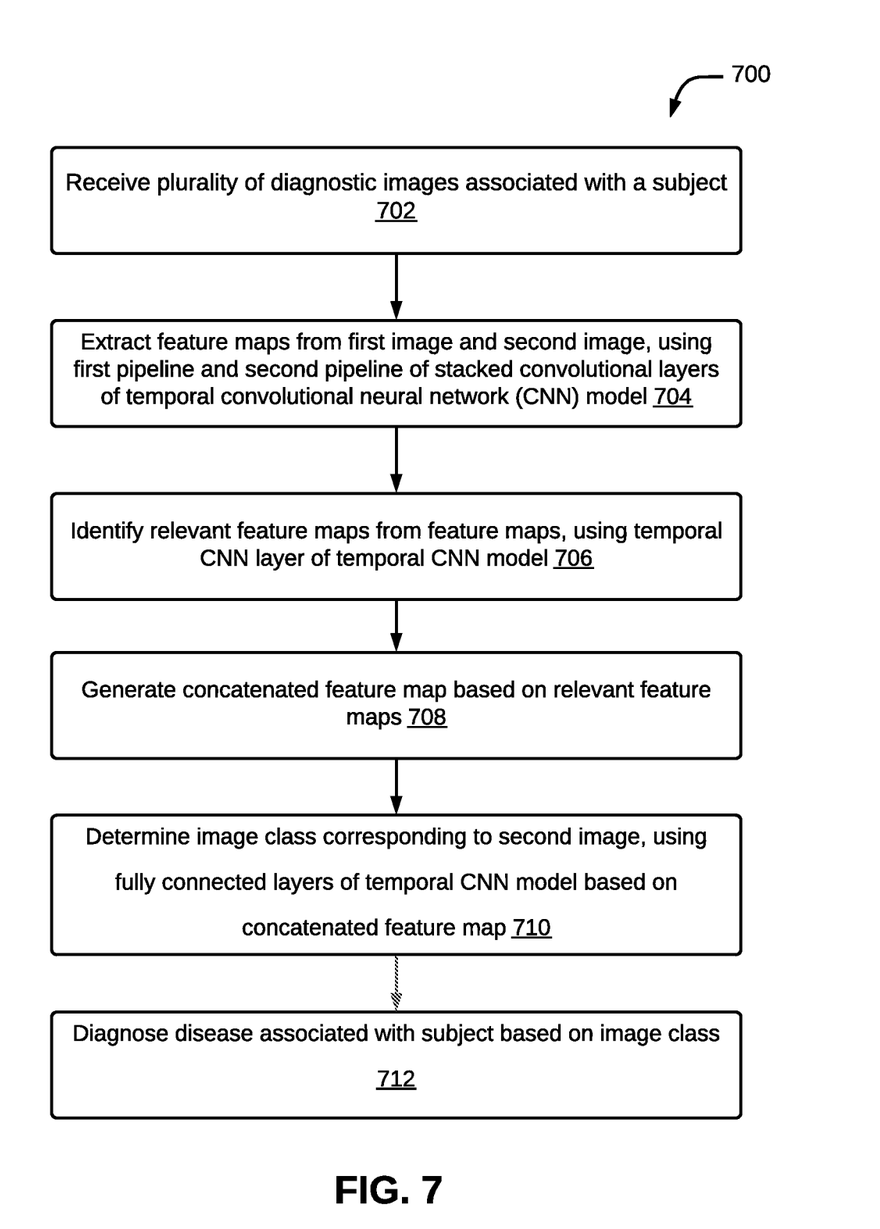
FIG. 7 is a flowchart that illustrates an exemplary method for diagnosing a disease using image classification, in accordance with an embodiment of the disclosure.

FIG. 7 is a flowchart that illustrates an exemplary method for diagnosing a disease using image classification, in accordance with an embodiment of the disclosure. With reference to FIG. 7, there is shown a flowchart 700. The operations of the exemplary method may be executed by any computing system, for example, by the disease diagnosis system 102 of FIG. 1. The operations of the flowchart 700 may start at 702 and proceed to 704.

At 702, a plurality of diagnostic images associated with a subject may be received. In accordance with an embodiment, the data acquisition module 404 of the disease diagnosis system 102 may be configured to receive the plurality of diagnostic images associated with the subject. The plurality of diagnostic images may include a first image captured at a first instance of time and a second image captured at a second instance of time.

In accordance with an embodiment, the first image may correspond to a normal image. The normal image may be captured at the first instance of time. In accordance with an embodiment, the second image may correspond to a decision image. The decision image may be captured at the second instance of time. Further, the first image and the second image may be sent to the temporal CNN module 406 for further processing at 704. In accordance with an embodiment, the plurality of diagnostic images may include at least one of X-ray images, computed tomography (CT) scan images, positron emission tomography (PET) scan images, microscopy images, and temporally differing images.

At 704, feature maps from the first image and the second image may be extracted using a first pipeline of stacked convolutional layers of a temporal convolutional neural network (CNN) model and a second pipeline of the stacked convolutional layers of the temporal CNN model respectively. In accordance with an embodiment, the temporal CNN module 406 may be configured to extract the feature maps from the first image and the second image, using the first pipeline of stacked convolutional layers of the temporal convolutional neural network (CNN) model and the second pipeline of the stacked convolutional layers of the temporal CNN model respectively.

The temporal CNN model may be trained on a plurality of training images to learn temporal differences among the normal class, the infected class, and the inconclusive class from the plurality of training images. In accordance with an embodiment, the stacked convolutional layers of the temporal CNN model may be trained in a frozen state using transfer learning algorithm.

At 706, relevant feature maps may be extracted from the feature maps, using a temporal CNN layer of the temporal CNN model. In accordance with an embodiment, the temporal CNN module 406 may be configured to identify the relevant feature maps from the feature maps. In accordance with an embodiment, for identifying the relevant feature maps from the feature maps, the temporal CNN module 406 may be configured to generate relevance values for features in the feature maps of the first image and the second image. The features corresponding to relevance values below a threshold value may be discarded. The features corresponding to the relevance values above the threshold value may be considered as relevant feature maps.

In accordance with an embodiment, the threshold value may be determined during a training phase of the temporal CNN model. In accordance with an embodiment, the relevance values may be generated for the features in the feature maps of the first image and the second image, using Layer Wise Relevance Propagation (LRP) algorithm. In accordance with an embodiment, the temporal CNN module 406 may be configured to sort the relevant feature maps based on a selection of the relevant features above the threshold value. In accordance with an embodiment, a relative relevance may be computed at any layer of the temporal convolutional neural network model by appropriately distributing relevance among different neurons.

At 708, a concatenated feature map may be generated based on the relevant feature maps. In accordance with an embodiment, the temporal CNN module 406 may be configured to generate the concatenated feature map based on the relevant feature maps. The concatenated feature map may correspond to a temporal difference between the first image and the second image.

At 710, an image class corresponding to the second image may be determined, using a fully connected layers of the temporal CNN model, based on the concatenated feature map. In accordance with an embodiment, the temporal CNN module 406 may be configured to determine an image class corresponding to the second image, using a fully connected layers of the temporal CNN model. The image class corresponding to the second image may be determined, based on the concatenated feature map. The image class may correspond to at least one of a normal class, an infected class, or an inconclusive class.

In accordance with an embodiment, for determining the image class, the temporal CNN module 406 may be configured to compare the concatenated feature map with stored feature maps corresponding to each of the predefined diagnostic class (either normal class or infected class). Based on comparison, the temporal CNN module 406 may be configured to categorize the second image into one of the image class. If the detected class is "infected" then the image is fed to the diagnostic type prediction unit for further processing.

At 712, a disease associated with the subject may be diagnosed based on the image class. In accordance with an embodiment, the temporal CNN module 406 may be configured to diagnose the disease associated with the subject based on the image class. Additionally, or alternatively, the diagnostic prediction module 408 may be configured to diagnose the disease associated with the subject by detecting a type of the image class, based on the determination of the image class. Further, the diagnostic prediction module 408 determine the type of infection using a trained CNN model as described in FIG. 6.

In accordance with an embodiment, the rendering module 410 may be configured to render a diagnosis report on a user device. The diagnosis report may include the image class and one of: the disease when the image class may correspond to the infected class, and a recommendation when the image class may correspond to the inconclusive class. In accordance with an embodiment, data associated with the diagnosis report may be extracted from the data repository 412.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It will be appreciated that, for clarity purposes, the above description has described embodiments of the disclosure with reference to different functional units and processors. However, it will be apparent that any suitable distribution of functionality between different functional units, processors or domains may be used without detracting from the disclosure. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Although the present disclosure has been described in connection with some embodiments, it is not intended to be limited to the specific form set forth herein. Rather, the scope of the present disclosure is limited only by the claims. Additionally, although a feature may appear to be described in connection with particular embodiments, one skilled in the art would recognize that various features of the described embodiments may be combined in accordance with the disclosure.

Furthermore, although individually listed, a plurality of means, elements or process steps may be implemented by, for example, a single unit or processor. Additionally, although individual features may be included in different claims, these may possibly be advantageously combined, and the inclusion in different claims does not imply that a combination of features is not feasible and/or advantageous. Also, the inclusion of a feature in one category of claims does not imply a limitation to this category, but rather the feature may be equally applicable to other claim categories, as appropriate.

What is claimed is:

1. A system for diagnosing a disease using image classification, the system comprising:
a processor; and
a memory communicatively coupled to the processor, wherein the memory is configured to store a temporal convolutional neural network (CNN) model, a plurality of diagnostic images associated with a subject, and processor-executable instructions, wherein the processor-executable instructions, on execution, cause the processor to:
input a first image of the plurality of diagnostic images captured at a first instance of time to a first pipeline of stacked convolutional layers of the temporal CNN model and a second image of the plurality of diagnostic images captured at a second instance of time to a second pipeline of the stacked convolutional layers of the temporal CNN model, wherein the first pipeline and the second pipeline of the stacked convolutional layers are configured to extract feature maps from the first image and the second image respectively;
input the feature maps extracted from the first pipeline and the second pipeline to a temporal CNN layer of the temporal CNN model, wherein the temporal CNN layer is configured to identify relevant feature maps from the feature maps and to generate a concatenated feature map based on the relevant feature maps, wherein the concatenated feature map corresponds to a temporal difference between the first image and the second image;
input the concatenated feature map from the temporal CNN layer to fully connected layers of the temporal CNN model, wherein the fully connected layers are configured to determine an image class corresponding to the second images based on the concatenated feature map, wherein the image class corresponds to at least one of a normal class, an infected class, or an inconclusive class; and
diagnosing a disease associated with the subject based on the image class.

2. The system of claim 1, wherein the temporal CNN model is trained on a plurality of training images to learn temporal differences among the normal class, the infected class, and the inconclusive class from the plurality of training images.

3. The system of claim 2, wherein the stacked convolutional layers of the temporal CNN model are trained in a frozen state using transfer learning algorithm.

4. The system of claim 1, wherein the processor-executable instructions, on execution, further cause the processor to render a diagnosis report on a user device, wherein the diagnosis report comprises the image class and one of: the disease when the image class corresponds to the infected class, and a recommendation when the image class corresponds to the inconclusive class.

5. The system of claim 1, wherein to identify the relevant feature maps, the processor-executable instructions, on execution, cause the processor to generate relevance values for features in the feature maps of the first image and the second image, wherein the features corresponding to the relevance values below a threshold value are discarded, wherein the threshold value is determined during a training phase of the temporal CNN model.

6. The system of claim 5, wherein to generate the relevance values, the processor-executable instructions, on execution, cause the processor to employ Layer Wise Relevance Propagation (LRP) algorithm.

7. The system of claim 5, wherein to generate the concatenated feature map, the processor-executable instructions, on execution, cause the processor to sort the relevant feature maps based on a selection of the relevant features above the threshold value.

8. The system of claim 1, wherein the plurality of diagnostic images comprises at least one of X-ray images, computed tomography (CT) scan images, positron emission tomography (PET) scan images, microscopy images, and temporally differing images.

9. A method of diagnosing a disease using image classification, the method comprising:
   receiving, by a system for diagnosing diseases using image classification, a plurality of diagnostic images associated with a subject, wherein the plurality of diagnostic images comprises a first image captured at a first instance of time and a second image captured at a second instance of time;
   extracting, by the system, feature maps from the first image and the second image, using a first pipeline of stacked convolutional layers of a temporal convolutional neural network (CNN) model and a second pipeline of the stacked convolutional layers of the temporal CNN model respectively;
   identifying, by the system, relevant feature maps from the feature maps, using a temporal CNN layer of the temporal CNN model;
   generating, by the system, a concatenated feature map based on the relevant feature maps, wherein the concatenated feature map corresponds to a temporal difference between the first image and the second image;
   determining, by the system, an image class corresponding to the second image, using a fully connected layers of the temporal CNN model, based on the concatenated feature map, wherein the image class corresponds to at least one of a normal class, an infected class, or an inconclusive class; and
   diagnosing, by the system, a disease associated with the subject based on the image class.

10. The method of claim 9, wherein the temporal CNN model is trained on a plurality of training images to learn temporal differences among the normal class, the infected class, and the inconclusive class from the plurality of training images.

11. The method of claim 10, wherein the stacked convolutional layers of the temporal CNN model are trained in a frozen state using transfer learning algorithm.

12. The method of claim 9, further comprising rendering a diagnosis report on a user device, wherein the diagnosis report comprises the image class and one of: the disease when the image class corresponds to the infected class, and a recommendation when the image class corresponds to the inconclusive class.

13. The method of claim 9, wherein identifying the relevant feature maps comprises generating relevance values for features in the feature maps of the first image and the second image, wherein the features corresponding to relevance values below a threshold value are discarded, wherein the threshold value is determined during a training phase of the temporal CNN model.

14. The method of claim 13, wherein generating the relevance values comprises generating the relevance values for the features in the feature maps of the first image and the second image, using Layer Wise Relevance Propagation (LRP) algorithm.

15. The method of claim 13, wherein generating the concatenated feature map comprises sorting the relevant feature maps based on a selection of the relevant features above the threshold value.

16. A non-transitory computer-readable medium storing computer-executable instructions for diagnosing a disease using image classification, the computer-executable instructions configured for:
   receiving a plurality of diagnostic images associated with a subject, wherein the plurality of diagnostic images comprises a first image captured at a first instance of time and a second image captured at a second instance of time;
   extracting feature maps from the first image and the second image, using a first pipeline of stacked convolutional layers of a temporal convolutional neural network (CNN) model and a second pipeline of the stacked convolutional layers of the temporal CNN model respectively;
   identifying relevant feature maps from the feature maps, using a temporal CNN layer of the temporal CNN model;
   generating a concatenated feature map based on the relevant feature maps, wherein the concatenated feature map corresponds to a temporal difference between the first image and the second image;
   determining an image class corresponding to the second image, using a fully connected layers of the temporal CNN model, based on the concatenated feature map, wherein the image class corresponds to at least one of a normal class, an infected class, or an inconclusive class; and
   diagnosing a disease associated with the subject based on the image class.

17. The non-transitory computer-readable medium of the claim 16, wherein the temporal CNN model is trained on a plurality of training images to learn temporal differences among the normal class, the infected class, and the inconclusive class from the plurality of training images, and wherein the stacked convolutional layers of the temporal CNN model are trained in a frozen state using transfer learning algorithm.

18. The non-transitory computer-readable medium of the claim 16, wherein the computer-executable instructions are further configured for rendering a diagnosis report on a user device, wherein the diagnosis report comprises the image class and one of: the disease when the image class corresponds to the infected class, and a recommendation when the image class corresponds to the inconclusive class.

19. The non-transitory computer-readable medium of the claim 16, wherein to identify the relevant feature maps, the computer-executable instructions are further configured for generating relevance values for features in the feature maps of the first image and the second image using Layer Wise Relevance Propagation (LRP) algorithm, wherein the features corresponding to relevance values below a threshold value are discarded, wherein the threshold value is determined during a training phase of the temporal CNN model.

20. The non-transitory computer-readable medium of the claim 19, wherein to generate the concatenated feature map, the computer-executable instructions are further configured for sorting the relevant feature maps based on a selection of the relevant features above the threshold value.

* * * * *